United States Patent
Abraham et al.

(10) Patent No.: US 8,933,292 B2
(45) Date of Patent: *Jan. 13, 2015

(54) ABSORBENT ARTICLE WITH SENSOR ARRAY FOR BODY EXUDATE DETECTION

(75) Inventors: Jose K. Abraham, Neenah, WI (US); Kathy Geralyn Richardson, Combined Locks, WI (US); Davis Dang Hoang Nhan, Appleton, WI (US); Theodore T. Tower, Appleton, WI (US); Candace Dyan Krautkramer, Neenah, WI (US); John Gavin MacDonald, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 476 days.

This patent is subject to a terminal disclaimer.

(21) Appl. No.: 13/283,651

(22) Filed: Oct. 28, 2011

(65) Prior Publication Data

US 2013/0110063 A1     May 2, 2013

(51) Int. Cl.
*A61F 13/42*     (2006.01)
*G08B 21/20*     (2006.01)

(52) U.S. Cl.
CPC ............... *A61F 13/42* (2013.01); *G08B 21/20* (2013.01); *A61F 2013/424* (2013.01)
USPC ........................................................ 604/361

(58) Field of Classification Search
CPC .... A61F 13/42; A61F 2013/424; G08B 21/20
USPC ........................................................ 604/361
See application file for complete search history.

(56) References Cited

U.S. PATENT DOCUMENTS

| | | | |
|---|---|---|---|
| 4,100,324 A | 7/1978 | Anderson et al. |
| 4,704,116 A | 11/1987 | Enloe |
| 4,887,455 A | 12/1989 | Payne et al. |
| 4,940,464 A | 7/1990 | Van Gompel et al. |
| 5,284,703 A | 2/1994 | Everhart et al. |
| 5,350,624 A | 9/1994 | Georger et al. |
| 5,486,166 A | 1/1996 | Bishop et al. |
| 5,490,846 A | 2/1996 | Ellis et al. |

(Continued)

FOREIGN PATENT DOCUMENTS

| | | |
|---|---|---|
| EP | 1092151 B1 | 10/2008 |
| JP | 9290001 A | 11/1997 |

(Continued)

OTHER PUBLICATIONS

Search Report and Written Opinion for PCT/IB2012/055074 dated Feb. 25, 2013, 12 pages.

(Continued)

*Primary Examiner* — Susan Su
(74) *Attorney, Agent, or Firm* — Dority & Manning, P.A.

(57) ABSTRACT

An absorbent article incorporating a non-contact electronic sensor array that may indicate the presence of a body exudate is disclosed. In particular, the absorbent article includes at least a non-contact electronic sensor array that may include one or more gas sensors, a controller and a signaling device. The signaling device is capable of alerting a user (wearer or caregiver) that an insult of urine or bowel movement has occurred. In accordance with the present disclosure, various attachment mechanisms are disclosed for attaching the non-contact electronic sensor array, controller and signaling device to an absorbent article.

18 Claims, 6 Drawing Sheets

(56) References Cited

U.S. PATENT DOCUMENTS

| | | |
|---|---|---|
| 5,709,222 A | 1/1998 | Davallou |
| 5,766,389 A | 6/1998 | Brandon et al. |
| 5,820,973 A | 10/1998 | Dodge, II et al. |
| 5,876,393 A | 3/1999 | Ahr et al. |
| 6,093,869 A | 7/2000 | Roe et al. |
| 6,097,297 A | 8/2000 | Fard |
| 6,217,828 B1 | 4/2001 | Bretscher et al. |
| 6,236,951 B1 | 5/2001 | Payne et al. |
| 6,342,037 B1 | 1/2002 | Roe et al. |
| 6,399,853 B1 | 6/2002 | Roe et al. |
| 6,506,958 B2 | 1/2003 | Williams |
| 6,570,053 B2 | 5/2003 | Roe et al. |
| 6,575,013 B2 | 6/2003 | Bao et al. |
| 6,645,190 B1 | 11/2003 | Olson et al. |
| 6,683,228 B1 | 1/2004 | Pacheco, Sr. |
| 6,723,040 B2 | 4/2004 | Brady |
| 6,773,926 B1 | 8/2004 | Freund et al. |
| 6,840,069 B2 | 1/2005 | France et al. |
| 6,885,827 B2 | 4/2005 | Shushakov et al. |
| 6,966,840 B2 | 11/2005 | Nelson |
| 7,171,312 B2 | 1/2007 | Steinthal et al. |
| 7,176,344 B2 | 2/2007 | Gustafson et al. |
| 7,221,279 B2 | 5/2007 | Nielsen |
| 7,280,441 B2 | 10/2007 | MacDonald et al. |
| 7,335,168 B2 | 2/2008 | Rugg |
| 7,413,550 B2 | 8/2008 | MacDonald et al. |
| 7,449,614 B2 | 11/2008 | Ales, III |
| 7,477,156 B2 | 1/2009 | Long et al. |
| 7,489,252 B2 | 2/2009 | Long et al. |
| 7,498,478 B2 | 3/2009 | Long et al. |
| 7,582,485 B2 | 9/2009 | Boga et al. |
| 7,592,020 B2 | 9/2009 | Boga et al. |
| 7,667,608 B2 | 2/2010 | Ales et al. |
| 7,700,821 B2 | 4/2010 | Ales, III et al. |
| 7,705,194 B2 | 4/2010 | Underhill et al. |
| 7,737,322 B2 | 6/2010 | Ales, III et al. |
| 7,757,478 B2 | 7/2010 | Wang et al. |
| 7,760,101 B2 | 7/2010 | Ales, III et al. |
| 7,763,912 B2 | 7/2010 | Kasama et al. |
| 7,800,505 B2 | 9/2010 | Pietersen |
| 7,834,235 B2 | 11/2010 | Long et al. |
| 7,837,663 B2 | 11/2010 | MacDonald et al. |
| 7,837,845 B2 | 11/2010 | Abel et al. |
| 7,915,476 B2 | 3/2011 | Long et al. |
| 7,973,210 B2 | 7/2011 | Long et al. |
| 7,977,529 B2 | 7/2011 | Bergman et al. |
| 7,978,083 B2 | 7/2011 | Melker et al. |
| 8,093,998 B2 | 1/2012 | Grossman |
| 8,274,393 B2 | 9/2012 | Ales et al. |
| 8,299,317 B2 | 10/2012 | Tippey et al. |
| 8,394,074 B2 | 3/2013 | Piette et al. |
| 2003/0054326 A1 | 3/2003 | Aaron-Barrada |
| 2004/0147888 A1 | 7/2004 | Huang et al. |
| 2004/0220538 A1 | 11/2004 | Panopoulos |
| 2005/0136384 A1 | 6/2005 | Jarvis |
| 2005/0268962 A1 | 12/2005 | Gaudiana et al. |
| 2006/0223052 A1 | 10/2006 | MacDonald |
| 2007/0048709 A1 | 3/2007 | Ales, III et al. |
| 2007/0270774 A1* | 11/2007 | Bergman et al. ............... 604/361 |
| 2008/0058740 A1* | 3/2008 | Sullivan et al. ............... 604/361 |
| 2008/0255528 A1 | 10/2008 | Springer et al. |
| 2008/0268405 A1 | 10/2008 | Cohen et al. |
| 2008/0300650 A1 | 12/2008 | Gerber et al. |
| 2009/0089928 A1 | 4/2009 | Kasbohm |
| 2009/0155753 A1 | 6/2009 | Ales et al. |
| 2009/0157022 A1 | 6/2009 | MacDonald et al. |
| 2009/0221980 A1 | 9/2009 | Mosbacher et al. |
| 2009/0302498 A1 | 12/2009 | Nedestam |
| 2010/0030173 A1 | 2/2010 | Song et al. |
| 2010/0114046 A1* | 5/2010 | Ales et al. ..................... 604/361 |
| 2010/0121292 A1 | 5/2010 | Wakrim et al. |
| 2010/0133120 A1 | 6/2010 | Varney et al. |
| 2010/0164733 A1* | 7/2010 | Ales et al. ..................... 340/604 |
| 2010/0209898 A1 | 8/2010 | Ward |
| 2011/0025510 A1* | 2/2011 | Bunza et al. ............... 340/573.5 |
| 2011/0152806 A1 | 6/2011 | Zhou et al. |
| 2011/0263952 A1* | 10/2011 | Bergman et al. ............... 600/309 |
| 2012/0019388 A1* | 1/2012 | Kates ........................... 340/605 |
| 2012/0108465 A1 | 5/2012 | Duoss et al. |
| 2012/0227983 A1 | 9/2012 | Lymberopoulos et al. |

FOREIGN PATENT DOCUMENTS

| | | |
|---|---|---|
| JP | 2000093447 A | 4/2000 |
| JP | 2003090812 A | 3/2003 |
| JP | 2007024850 A | 2/2007 |
| KR | 2010004473 U | 4/2010 |
| WO | WO 9830179 A1 | 7/1998 |
| WO | WO 0037009 A2 | 6/2000 |
| WO | WO 0249561 A1 | 6/2002 |
| WO | WO 2007073139 A1 | 6/2007 |

OTHER PUBLICATIONS

Abstract of Japanese Patent—JP9187431 dated Jul. 22, 2997, 2 pages.
Abstract of Japanese Patent—JP2004139545 dated May 13, 2004, 2 pages.
Abstract of Japanese Patent—JP2005245695 dated Sep. 15, 2005, 2 pages.
Abstract of Korean Patent—KR20090057001 dated Jun. 3, 2009, 1 page.
Arshak et al., "A review of gas sensors employed in electronic nose applications," *Sensor Review*, vol. 24, No. 2, 2004, pp. 181-198.
Garner et al. "Volatile organic compounds from feces and their potential for diagnosis of gastrointestinal disease," *The FASEB Journal*, vol. 21 Jun. 2007, pp. 1675-1688.
Machine Translation of Japanese Patent No. 2003-090812, Mar. 28, 2003, 9 pages.
Machine Translation of Japanese Patent No. 3147110, Dec. 18, 2008, 14 pages.
Machine Translation and English Abstract of Korean Patent No. 20090006641 (200449196, 2 pages), Jul. 2, 2009, 6 pages.
Machine Translation and English Abstract of Korean Patent No. 20110008902, Jan. 27, 2011, 6 pages.
Related U.S. Patent Applications Form.

* cited by examiner

ABSORBENT ARTICLE WITH SENSOR ARRAY FOR BODY EXUDATE DETECTION

BACKGROUND

Absorbent articles such as diapers, training pants, incontinence products, feminine hygiene products, swim undergarments, bed pads, and the like conventionally include a liquid permeable body-side liner, a liquid impermeable outer cover, and an absorbent core. The absorbent core is typically located in between the outer cover and the liner for taking in and retaining urine, bowel movements, and other body exudates exuded by the wearer.

The absorbent core can be made of, for instance, superabsorbent particles. Many absorbent articles, especially those sold under the tradename HUGGIES™ by the Kimberly-Clark Corporation, are so efficient at absorbing liquids that it is sometimes difficult to tell whether or not the absorbent article has been insulted with a body exudate such as urine or bowel movement.

Accordingly, various types of moisture, wetness or bowel movement indicators have been suggested for use in absorbent articles in order to detect the presence of a urine or bowel movement insult within an absorbent article. These indicators may include alarm devices that are designed to assist parents or care-givers identify a wet or soiled diaper condition early on. The devices produce either a visual or an audible signal.

In some embodiments, a wetness indicator has been added to an absorbent article to detect urine insults, and in other embodiments, a sensor for odor detection has been added to detect bowel movement insults. In these embodiments, sensors using conductive materials are incorporated into the absorbent article where the urine insult or bowel movement insult must come into close contact with the sensing elements in order for the indicator to detect an insult. For example, the conductive materials serve as conductive leads for a signaling device and form an open circuit in the article that can be closed when a body fluid, such as urine, closes the circuit. In these embodiments, although the absorbent articles may be disposable, the signaling devices are not. Thus, the signaling devices are intended to be removed from the article and reattached to a subsequent article.

Problems, however, have been encountered in designing an absorbent article with conductive materials where the urine or bowel movement comes into sufficient contact with the conductive materials to close the open circuit. Further, problems have been experienced in including conductive materials such as metals within an absorbent article because such materials trigger metal detectors during the shipping process. Additionally, the use of conductive leads makes it difficult for manufacturers of absorbent articles to monitor their products from a safety standpoint. For example, it may be difficult to ensure consumers that a product is free of all other metals or other foreign objects with the exception of the conductive leads. Therefore, a need exists for an absorbent article that can detect both urine and bowel movement insults without the use of conductive leads.

Additionally, advances in absorbent article technology with the use of hydrophobic inner layer in absorbent articles permits urine to pass through the surface of the absorbent article so that it cannot come in contact with the skin, even after multiple insults. However, feces or bowel movements cannot be absorbed completely into any of these layers, meaning that prolonged contact with skin is inevitable. An electronic device that can detect body fluids such as urine and bowel movement components is highly desired, particularly for new users as well as users of adult care incontinent products. Since several of the prior arts to detect the presence of bowel movements are based on wetness sensing, they fail to discriminate between urine and bowel movements. This could mislead a user and adds an additional burden to an already overloaded caregiver. One of the challenges of the marketed indicators is that it cannot discriminate between bowel movement, sweat and passing gases. A sensor that can discriminate between urine and bowel movement would allow for a caregiver to react more quickly to changing an absorbent containing a bowel movement insult, where prolonged contact of the insult with the child's skin can be detrimental to the child's health.

SUMMARY

In general, the present disclosure is directed to an improved absorbent article including a non-contact electronic sensor array, a controller and a signaling device that alerts the user of urine and/or bowel movement insults. The signaling device, for instance, may be configured to indicate to a user (wearer or caregiver) that insults of urine and/or bowel movement are present in or on the absorbent article. For example, in one embodiment, the absorbent article comprises a diaper or training pant and the signaling device is configured to indicate the presence of urine, a bowel movement or both. In other embodiments, however, the signaling device may be configured to indicate the presence of yeast or metabolites depending upon the particular type of absorbent article that is used in conjunction with the signaling device.

In one embodiment, the absorbent article of the present disclosure may include a housing unit that may be configured to be reused. Thus, the present disclosure is directed to an absorbent article with a simple and efficient manner of attaching the housing unit to the absorbent article so that the non-contact electronic sensor array is in close enough proximity to an insult within the absorbent article in order to detect gases within an absorbent article, while at the same time maintaining communication with the controller and signaling device.

In another embodiment, the absorbent article may comprise a chassis. The chassis may further comprise an outer cover having an interior surface and an exterior surface. There may be an absorbent structure positioned adjacent to the interior surface of the outer cover. Further, the chassis may include a crotch region that is positioned in between a front region and a back region. The front region and the back region may define a waist opening and two leg openings between the front region and back region. However, the absorbent article may be a bed pad or mat rather than a diaper or training pant with a crotch region and leg openings.

The present disclosure may also include a non-contact electronic sensor array. The non-contact electronic sensor array may comprise a plurality of gas sensors. The sensor array can monitor gas concentration levels of gases emitted by two or more volatile compounds within the absorbent article.

In still another embodiment, a controller may be attached to the absorbent article. The controller can be configured to detect changes above a threshold level in the gas concentration levels of a plurality of gas sensors within the non-contact electronic sensor array as the result of an insult within the absorbent article. The insult may be urine, bowel movement, or combinations of both. The non-contact electronic sensor array can monitor gas concentration levels of gases associated with ammonia, indole, and thiols such as mercaptan. The non-contact electronic sensor array may also monitor other volatile compounds such short chain fatty acids, acetic acid, methane, hydrogen sulfide, skatole, or combinations thereof.

Gases can be measured from groups such as fatty alcohols (ethanol, propanol, octanol etc.), smaller chain fatty acids (acetic acid, propanoic acid, etc.) and sulfur compounds (dimethyl sulfide, indole, thiols, etc.). In another embodiment, the non-contact electronic sensor array can monitor changes in humidity and temperature within the absorbent article.

In yet another embodiment, a signaling device may be attached to the absorbent article. The signaling device may alert a user of changes in the gas concentration, temperature or humidity levels detected by the controller. The signaling device may generate an alert selected from an auditory signal, a vibratory signal, a visual signal, or combinations of the three alerts. The signaling device may generate an alert that is transmitted wirelessly to a radio at a remote location. In another embodiment, the signaling device can generate an alert that is transmitted to at least one computer device or smart phone. The alert may be deactivated at or near the absorbent article by the wearer or caregiver or remotely. The computer device or smart phone can be adapted to receive data from the signaling device, generate at least one report utilizing at least a portion of the data, and provide a user or caregiver access to the data and the at least one report.

In still another embodiment, the signaling device, controller, and non-contact electronic sensor array may be housed in a housing unit that can be attached to the absorbent article. The housing unit can be positioned in close proximity to absorbent article so that the non-contact electronic sensor array can detect gases within the interior of the absorbent article.

The absorbent article of the present disclosure may also comprise a gas emitting substance. The gas emitting substance can emit a gas after an insult within the absorbent article, and the non-contact electronic sensor array can monitor gas concentration levels of the gas emitting substance within the absorbent article.

In still another embodiment, an absorbent article may comprise a chassis that may have an outer cover with an interior surface and an exterior surface. There may be an absorbent structure positioned adjacent the interior surface of the outer cover. The chassis may also have a crotch region positioned in between a front region and a back region. The front region and back region may define a waist opening, and two leg openings may be between the front region and back region.

The present disclosure may also comprise a controller that can be configured to detect changes above a threshold level in the gas concentration levels of the plurality of gas sensors within the non-contact electronic sensor array as the result of an insult within the absorbent article, as well as changes in temperature and humidity. The insult may be urine, bowel movement, or combinations of both. In still another embodiment, the absorbent article may comprise a signaling device that alerts a user of changes in the gas concentration, temperature and humidity levels detected by the controller. The signaling device may generate an alert that is transmitted wirelessly to a radio at a remote location, it may generate an alert that is transmitted to at least one computer device or smart phone, or it may generate a combination of alerts. The alert may be deactivated at or near the absorbent article by the wearer or caregiver or remotely. The computer device or smart phone may be adapted to receive data from the signaling device, generate at least one report utilizing at least a portion of the data, and provide a user access to the data and the at least one report. The signaling device may also generate an alert selected from the group consisting of an auditory signal, a vibratory signal, a visual signal, and combinations thereof.

The absorbent article may further comprise a housing unit for the non-contact electronic sensor array, the controller and the signaling device. The housing unit can be connected to the absorbent article about the waist opening or edge of the absorbent article, depending upon the type of absorbent article being used, such as a diaper, training pant, or bed pad. For example, the housing unit may be positioned about the waist opening so that the non-contact electronic sensor array faces the interior of the absorbent article.

In another embodiment, the present disclosure describes a signaling device that may include a non-contact electronic sensor array. The non-contact electronic sensor array can include a plurality of gas sensors. The non-contact electronic sensor array monitors gas concentration levels of gases emitted by volatile compounds, a gas emitting substance, or combinations thereof within an absorbent article. The signaling device may also include a controller configured to detect changes above a threshold level in the gas concentration levels of the plurality of gas sensors within the non-contact electronic sensor array as the result of an insult within the absorbent article. The insult can be urine, bowel movement, or combinations thereof.

Additionally, the signaling device can alert a user of changes in the gas concentration levels detected by the non-contact electronic sensor array. The signaling device may be contained in a housing unit that is in close proximity to the absorbent article in order to detect changes in gas concentration levels within or on the absorbent article after an insult.

The signaling device may also generate at least one alert selected from an auditory signal, a vibratory signal, a visual signal, or combinations thereof. The signaling device can then transmit the at least one alert remotely to a radio, a computer device, a smart phone, or combinations thereof. The computer device or smart phone can be adapted to receive data from the signaling device, generate at least one report utilizing at least a portion of the data, and provide a user access to the data and the at least one report. The at least one alert can then be deactivated at or near the absorbent article or remotely.

Other features and aspects of the present disclosure are discussed in greater detail below.

BRIEF DESCRIPTION OF THE DRAWINGS

A full and enabling disclosure, including the best mode thereof to one of ordinary skill in the art, is set forth more particularly in the specification, including reference to the accompanying figures in which.

DETAILED DESCRIPTION

Figure 1:
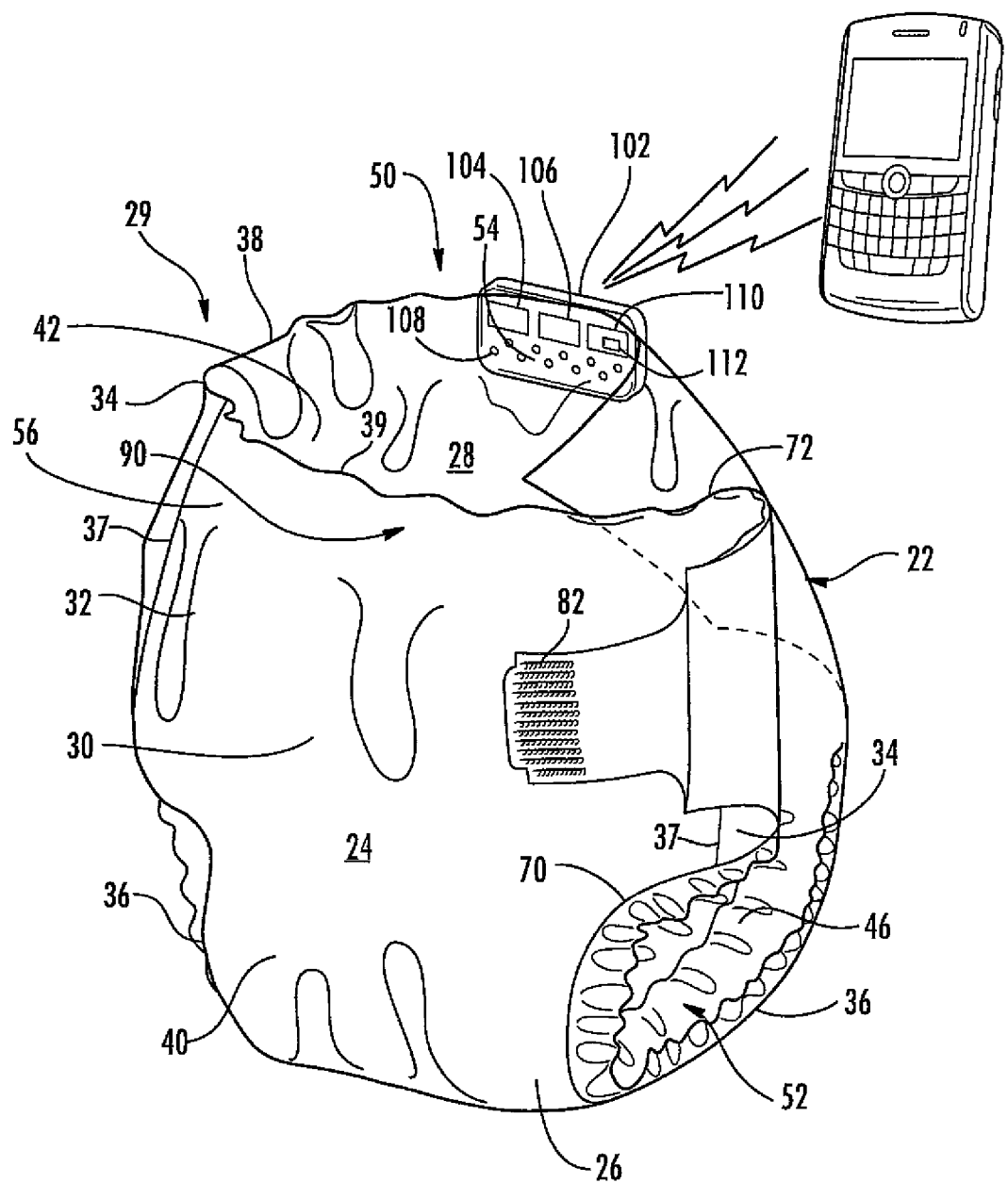
FIG. 1 is a perspective view of one embodiment of the present disclosure including one embodiment of a housing unit with non-contact electronic sensor array, controller and signaling device.

Reference will now be made in detail to various and alternative exemplary embodiments and to the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment can be used on another embodiment to yield a still further embodiment. Thus, it is intended that the present disclosure includes modifications and variations as come within the scope of the appended claims and their equivalents.

The present disclosure is generally directed to an absorbent article comprising a signaling device that may be configured to indicate the presence of a body exudate such as a urine or bowel movement insult in the absorbent article or other changes in the condition of the product or wearer, such as changes in temperature or humidity or the presence of malodor. The absorbent article may be, for instance, a diaper, a training pant, an incontinence product, a feminine hygiene product, a medical garment, a bandage, a bed pad or mat, and the like. An absorbent article made according to the present disclosure may include a non-contact electronic sensor array, a controller and a signaling device that may be contained within a housing unit that attaches, for example, at or near the waist opening of a diaper, a training pant or an incontinence product. The housing unit may also attach to an edge of any absorbent article, such as the edge of a bed mat, so long as the housing unit is in close enough proximity to the absorbent article to detect the gases associated with an insult. Generally, the absorbent article may be disposable, meaning that it is designed to be discarded after a limited use rather than being laundered or otherwise restored for reuse.

The non-contact electronic sensor array can be attached to the absorbent article of the present disclosure, although depending on the sensitivity of the sensors that may be used in the sensor array, attachment to the absorbent article may not be necessary. Additionally, the non-contact sensor array can be linked to a controller (microprocessor such as a multicomponent data analyzer) and a signaling device. The non-contact electronic sensor array, controller and signaling device may be contained within a single housing unit. The non-contact electronic sensor array may contain a plurality of gas sensors where each gas sensor monitors the level of gas emitted by a substance within the absorbent article. The gas may be emitted by a substance due to the presence of urine or bowel movement in the absorbent article.

Urine may contain inorganic salts, urea, organic compounds, or organic ammonium salts broken down into content of carbon, nitrogen, oxygen, hydrogen and organic sulfur. Bowel movement or feces may contain methane, dimethyl sulfide, indole, skatole, or short chain fatty acids, among other components. Contents of urine and feces may include volatile compounds. Such volatile compounds can be found within an absorbent article after an insult such as urine or bowel movement. The non-contact electronic sensor array can be composed of individual gas sensors that separately monitor such volatile compounds (VCs) as short chain fatty acids (acetic acid), ammonia, methane, hydrogen sulfide, dimethyl sulfide, skatole and indole. As used herein, the term "volatile compound" is meant to include both the organic and inorganic metabolic gases and compounds produced by microbes present in body wastes or exudates.

Particular VCs may be associated with one or more types of body exudates, including but not limited to urine and bowel movement. VCs commonly associated with urine include, for example, ammonia compounds (e.g., ammonia hydroxide), short chain ($C_1$-$C_2$) acids (e.g., acetic acid), medium length ($C_8$-$C_{10}$) aldehydes (e.g., nonanal), ketones (e.g., methyl ethyl ketone), cresol (e.g., methylphenol), dimethyl disulfide, trimethylamine, limonene (e.g., 4-isopropenyl-1-methylcyclohexane), acetic acid, methyl benzoate, benzamide, benzaldehyde, and triethylamine, among others. VCs commonly associated with bowel movement or feces include, for example, skatole (e.g., 3-methyl-1H-indole, 3-methylindole, etc.), mercaptans (e.g., 2-mercaptoethanol), hydrogensulfide, short chain fatty acids (e.g., myristic acid), methanethiol (e.g., 2-mercaptoethanol), and dimethylsulfide, among others. Some of the most common VCs in bowel movement or feces include short chain fatty acids, indole and dimethyl sulfide. Other VCs in bowel movement or feces include but are not limited to 4-methylphenol, pentanoic acid, 2- or 3-methylfuran, carbon disulfide, butanoic acid, ethanoic acid, 6-methyl-5-hepten-2-one, 2-pentanone 2-butanone, 2,3-butanedione, acetaldehyde, acetone, 2-heptanone, propanal, hexanal, and 3-methy.

The absorbent article may also contain a gas emitting substance that emits a gas when a urine or bowel movement insult occurs, and the non-contact electronic sensor array may be composed of at least one gas sensor that monitors the gas emitted from the gas-emitting substance. One advantage of the addition of a gas emitting substance is that the volume of gas produced immediately after an insult may be so high that an insult can be detected more quickly than when gases only associated with an insult or present. Gases associated with a urine or bowel movement insult may not be present in quantities as large as associated with the gas emitting substance, which could cause detection of the insult to take a longer amount of time.

For example, sodium bicarbonate or another substance that can emit a gas may be placed within the absorbent article during the manufacturing process or at some other time before the absorbent article is used by the consumer. The substances that may be included in the absorbent article can be in the form of powders, particles, flakes, fibers, agglomerates, granules, spheres, tablets, or lotions and may or may not be encapsulated. The materials can be incorporated into the absorbent article itself such as into the absorbent core or in a material such as a panty liner that may be added to the absorbent article at a later time. Upon the occurrence of a urine or bowel movement insult, the sodium bicarbonate or other substance such as a bicarbonate/citric acid powder mix can emit a gas, and the non-contact electronic sensor array can contain a sensor capable of monitoring the level of that gas. A microencapsulated film inside the absorbent article can also be used to emit a gas that can be detected by the sensors in the non-contact electronic sensor array. Water soluble films such as polyvinyl alcohol and polysaccharide film, available from MonoSol, LLC in Merrillville, Ind., can be used to encapsulate volatile substances such as a fragrant or menthol. These encapsulated materials can be placed in the absorbent article, and when wet, the film can be dissolved and release volatile substance that can be detected by the non-contact electronic sensor array. The processes by which the gas emitting substance can be incorporated into an absorbent article are described in U.S. Patent Application 2011/0152806A1 published Jun. 23, 2011 by Zhou, et al. Additionally, the controller can be programmed to recognize a gas level of the substance above a threshold level that can indicate the presence of a urine or bowel movement insult within the absorbent article. In another embodiment, the non-contact gas-sensor array can monitor the temperature and humidity within the absorbent article. The sensors that monitor temperature and humidity can be used alone or in combination with each other and the other sensors used for monitoring VCs.

A non-contact electronic sensor array and controller combination can be described as an array of sensors that may be of varying specificity in order to monitor VCs that could be present in a gas sample. An array of sensors or possibly a single device may detect particular odors, and then a controller such as a microprocessor uses pattern recognition to identify particular odors within a sample. The gas sample comes into contact with the sensor array, where each sensor in the array has the ability to identify a gas associated with particular substances. More than one sensor can be grouped in an array so that the controller can discriminate between various gases detected by various sensors, which may require a high level of independence amongst the sensors and how they operate to monitor a gas because of cross-correlation and redundancy. The sensors can be conductivity sensors, piezoelectric sensors, optical sensors or metal oxide semiconductor (MOS) sensors. MOS sensors are commercially available and are often used because of their high sensitivity to a wide range of organic compounds and gases. However, other types of sensors are also commercially available, including but not limited to those mentioned above.

One way in which a sensor works is that when a sample of a particular gas comes into contact with a sensor designed to monitor that gas, the sensor undergoes a physical or chemical change. This, in turn, causes a change in an electrical signal, which may be detected by a controller. The controller can be pre-conditioned to recognize that certain patterns are associated with certain gases, and it is thus able to detect gases associated with urine insults, bowel movement insults or other substances within an absorbent article.

Determining what sensors to use in the non-contact electronic sensor array depends on the substances to be detected. Individual sensors designed to measure gas concentration levels associated with particular VCs or other substances can be selected. These sensors can then be arranged within a non-contact electronic sensor array so that more than one gas can be monitored at a time. The suitability of a particular sensor material for monitoring a VC, another gas-emitting substance, temperature or humidity can be easily and readily determined by one skilled in the art based in part on the disclosure herein.

The controller can read gas levels monitored by the gas sensors in the non-contact electronic sensor array and analyze the data to identify a urine insult, a bowel movement insult, the presence of another gas-emitting substance upon the occurrence of a urine or bowel movement insult, or changes in humidity or temperature within the absorbent article. The controller can first read initial gas concentration levels monitored or detected by the non-contact electronic sensor array. These levels can then be calibrated to reflect a null value or zero, and then any change from these calibrated values is monitored. If a change in gas concentration levels, temperature or humidity above a certain threshold occurs, the controller may trigger an alarm through a signaling device.

The signaling device can provide power to the controller while also including an audible, visible and/or vibratory signal or alert that indicates to the user the presence of a urine insult or bowel movement insult. Any alerts from the signaling device can also be remotely activated or displayed on smart phones or computers. In another embodiment, an alert may also be sent to a wireless radio. In yet another embodiment, the alert may be sent to an indicator or display on the housing unit or some other area near the absorbent article so that the wearer can be alerted of an insult. The alerts can be deactivated remotely or at or near the signaling device itself. As alerts may be visual, auditory, vibratory or sent remotely to a computer device or smart phone, a caregiver can modify the type of alarm based on the level of discreteness that is desired. For example, if the caregiver is at home with the wearer of the article, it may be more appropriate to have an auditory alert, while if the caregiver and wearer are in a public place, a remote alert sent to a smart phone or a silent alert such as a visual alert may be more appropriate. Although the absorbent article itself is typically disposable, the signaling device may be reusable from article to article. In this regard, the present disclosure is particularly directed to the non-contact electronic sensor array, the controller, the signaling device and the attachment mechanisms that allow easy connection between the non-contact electronic sensor array, the controller, the signaling device and the absorbent article. For example, the non-contact electronic sensor array, the controller and the signaling device can all be contained within a single housing unit that attaches to the waist opening of a diaper or training pant or the edge of an absorbent article such as a bed mat via the use of a clip-on or other device.

The housing unit may be connected at or near the waist opening of the absorbent article via a clip on device or other means, where the non-contact electronic sensor array may face the interior of the absorbent article. If the non-contact electronic sensor array is part of an embodiment that includes a housing unit, small holes can be located on the housing unit in a manner that results in the holes being exposed to the interior of an absorbent article to allow for sufficient gas sampling by the non-contact electronic sensor array. Alternatively, the housing unit may be connected to the absorbent article via other means, so long as it is possible for the non-contact electronic sensor array portion to be in close enough proximity to the interior of the absorbent article to detect gases within the absorbent article. For example, the housing unit may be clipped or connected to the edge of a bed pad or mat.

As described above, the non-contact electronic sensor array in combination with the signaling device may be configured to indicate the presence of a urine or bowel movement insult within an absorbent article. However, the particular targeted insult may vary depending upon the particular type of absorbent article and the desired application. For instance, in one embodiment, the absorbent article comprises a diaper, a training pant, or the like and the signaling device is configured to indicate the presence of urine. Alternatively, the signaling device may be configured to indicate the presence of a volatile compound that would indicate the presence of a solid bowel movement or fluid-like bowel movement. Further still, the signaling device may be configured to indicate the presence of both urine and bowel movement, which can be more fluid-like than solid based on the age, diet or other traits of the wearer of the absorbent article.

Referring to FIG. 1 for exemplary purposes, an absorbent article 20 that may be made in accordance with the present disclosure is shown. The absorbent article 20 may or may not be disposable. It is understood that the present disclosure is suitable for use with various other absorbent articles intended for personal wear, including but not limited to diapers, training pants, swim pants, feminine hygiene products, incontinence products, medical garments, surgical pads and bandages, bed pads or mats, other personal care or health care garments, and the like without departing from the scope of the present disclosure, although only an absorbent article in the form of a diaper, training pant, or incontinence product may be shown. By way of illustration only, various materials and methods for constructing absorbent articles such as the absorbent article 20 of the various aspects of the present disclosure are described in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

An absorbent article 20 is representatively illustrated in FIG. 1 in a partially fastened condition. The absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the absorbent article 20, which when worn, wholly or partially cover or encircle the waist or mid-lower torso of the wearer. The crotch region 26 generally is that portion of the absorbent article 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated absorbent article 20 includes a chassis 32 that, in this embodiment, encompasses the front region 22, the back region 24, and the crotch region 26. Note, however, that other absorbent articles such as bed mats may be used instead. Referring to FIG. 1, the chassis 32 includes an outer cover 40 and a bodyside liner 42 that may be joined to the outer cover 40 in a superimposed relation therewith by adhesives, ultrasonic bonds, thermal bonds or other conventional techniques. Referring to FIG. 1, the liner 42 may suitably be joined to the outer cover 40 along the perimeter of the chassis 32 to form a front waist seam and a back waist seam. The liner 42 may suitably be joined to the outer cover 40 to form a pair of side seams in the front region 22 and the back region 24. The liner 42 can be generally adapted, i.e., positioned relative to the other components of the article 20, to be disposed toward the wearer's skin during wear of the absorbent article. The chassis 32 may further include an absorbent structure disposed between the outer cover 40 and the bodyside liner 42 for absorbing liquid or solid body exudates exuded by the wearer, and may further include a pair of containment flaps 46 secured to the bodyside liner 42 for inhibiting the lateral flow of body exudates.

The elasticized containment flaps 46 as shown in FIG. 1 define a partially unattached edge which assumes an upright configuration in at least the crotch region 26 of the absorbent article 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the absorbent article 20 may also suitably include leg elastic members (not shown), as are known to those skilled in the art. The leg elastic members can be operatively joined to the outer cover 40 and/or the bodyside liner 42 and positioned in the crotch region 26 of the absorbent article 20.

The leg elastic members can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members may include a plurality of dry-spun coalesced multifilament spandex elastomeric threads sold under the trade name LYCRA and available from Invista, Wilmington, Del., U.S.A.

In some embodiments, the absorbent article 20 may further include a surge management layer (not shown) which may be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid or other waste that may be rapidly introduced into the absorbent structure of the article. Desirably, the surge management layer can rapidly accept and temporarily hold the liquid or other waste prior to releasing the liquid or other waste into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIG. 1, the absorbent article 20 may further include a pair of opposing elastic side panels 34 that are attached to the back region of the chassis 32. As shown particularly, the side panels 34 may be stretched around the waist and/or hips of a wearer in order to secure the garment in place. As shown in FIG. 1, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in FIG. 1, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIG. 1, the elastic side panels 34 may be connected by a fastening system to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the FIG. 1, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The elastic side panels 34 each have a longitudinal outer edge (not shown), a leg end edge 70 disposed toward the longitudinal center of the diaper 20, and waist end edges 72 disposed toward a longitudinal end of the absorbent article. The leg end edges 70 of the absorbent article 20 may be suitably curved and/or angled to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present disclosure. Ultimately, the side panels 34 are generally aligned with a waist region 90 of the chassis 32.

The fastening system may include laterally opposite first fastening components 82 adapted for refastenable engagement to corresponding second fastening components (not shown). In the embodiment shown in the figures, the first fastening component 82 is located on the elastic side panels 34, while the second fastening component may be located on the front region 22 of the chassis 32. In one aspect, a front or outer surface of each of the fastening components includes a plurality of engaging elements. The engaging elements of the first fastening components 82 are adapted to repeatedly engage and disengage corresponding engaging elements of the second fastening components to releasably secure the article 20 in its three-dimensional configuration.

The fastening components may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

The first fastening components 82 may include hook fasteners and the second fastening components may include complementary loop fasteners. Alternatively, the first fastening components 82 may include loop fasteners and the second fastening components may be complementary hook fasteners. In another aspect, the fastening components can be interlocking similar surface fasteners, or adhesive and cohesive fastening elements such as an adhesive fastener and an adhesive-receptive landing zone or material; or the like. One skilled in the art will recognize that the shape, density and polymer composition of the hooks and loops may be selected to obtain the desired level of engagement between the fastening components. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the embodiment shown in the figures, the fastening components 82 are attached to the side panels 34 along the edges. In this embodiment, the fastening components 82 are not elastic or extendable. In other embodiments, however, the fastening components may be integral with the side panels 34. For example, the fastening components may be directly attached to the side panels 34 on a surface thereof.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

Figure 2:
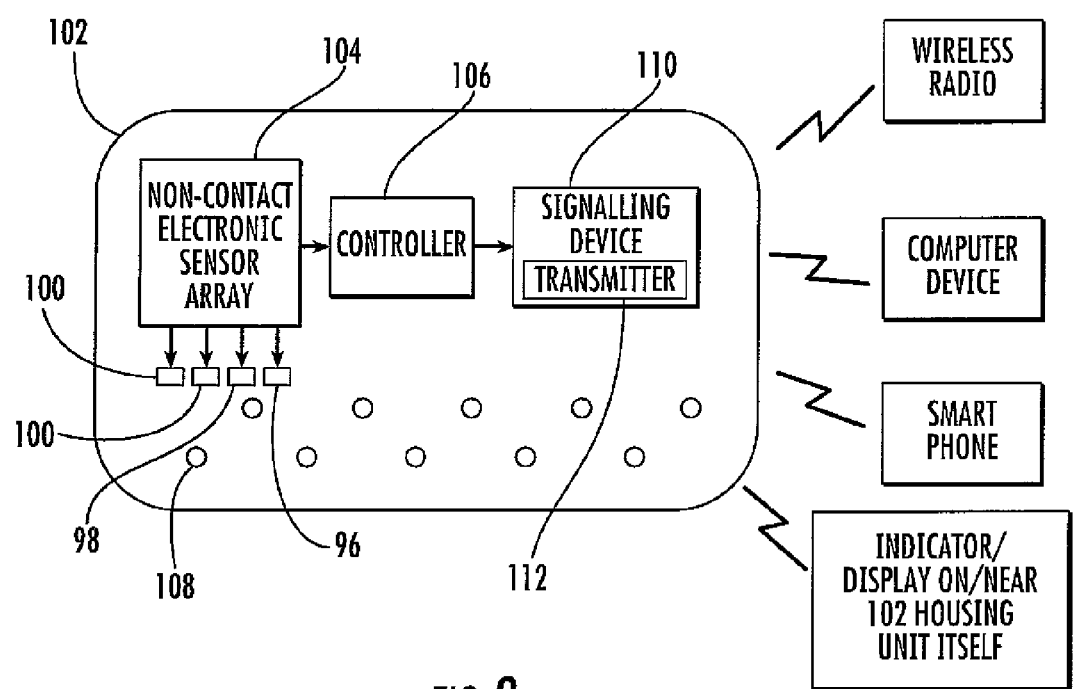
FIG. 2 is a block diagram of one embodiment of a housing unit which may contain a non-contact electronic sensor array, a controller and a signaling device that may be located at or near the waist opening of an absorbent article or may transmit a signal to a radio, a computer device, a smart phone or indicator/display that is on or near the housing unit.

Referring to FIGS. 1 and 2, for exemplary purposes, a housing unit 102 that contains, for example, a non-contact electronic sensor array 104, a controller 106 and a signaling device 110 is shown attached to the absorbent article 20. In this embodiment, the signaling device generally 110 includes a transmitter 112 that communicates with a receiver 114. The receiver can be a radio, a computer device or a smart phone. The transmitter 112 can be housed in the housing unit 102 with the non-contact electronic sensor array 104 and controller 106. When an insult is present in or on the absorbent article 20, the controller 106 detects changes in gas levels monitored by the non-contact electronic sensor array 104, which, in turn, activates the signaling device 110. In one embodiment, the non-contact electronic sensor array is able to monitor gas levels through visible openings 108 in the housing unit 102. In another embodiment, it is possible that the housing unit could be constructed of a porous material so that a sufficient amount of gas could enter into the housing unit, to allow the non-contact electronic sensor array to detect the presence of any gases.

In still another embodiment, the transmitter 112 may send a wireless signal or alert to the receiver 114 which then indicates to a user that urine or bowel movement insult is present in the absorbent article. The signaling device 110 can emit an audible signal, a visual signal and/or a vibratory signal in order to indicate to the user that an insult has been detected. The audible signal, for instance, may be as simple as one or more beeps to perhaps emitting a musical tune. Similarly, if the signaling device 110 issues a visible signal, the visible signal may comprise a few lights or an interactive display. The signals or alerts may be deactivated remotely or at or near the opening of the absorbent article. In still another embodiment, the receiver 114 of the signaling device 110 may be configured to vibrate when an insult has been detected.

As described above, the signaling device 110 can be configured to indicate the presence of any insult within the absorbent article 20. The insult may comprise, for instance, urine and/or bowel movement, which may or may not be fluid-like. In the embodiment shown in FIGS. 1 and 2, the signaling device 110 includes a transmitter 112 in combination with a receiver 114. It should also be understood, however, that the signaling device may be a single unit that is located on or near the absorbent article 20. For example, the signaling device may be mounted on the absorbent article and issue a visible signal and/or an audible signal from the article itself so that the wearer or another person such as a caregiver who is close by can be notified of an insult. Additionally, it should be understood that data from the signaling device may be transmitted to a radio, computer or smartphone through a wireless network or other means.

In the embodiment shown in FIG. 2, the housing unit 102 that may be attached to the absorbent article contains a non-contact electronic sensor array 104 which could have a temperature sensor 96, a humidity sensor 98, at least one individual gas sensor 100, a controller 106 and a signaling device 110, which can include a transmitter 112 and a receiver 114. Additionally, openings 108 may be present on the signaling device that allow the non-contact electronic sensor array 104 to be exposed to a sufficient gas sample in order to detect in the presence of one or more gases. In another embodiment, a gas sample can reach the non-contact electronic sensor array by traveling through a housing unit made of a porous material. In yet another embodiment of a housing unit, if the signal is being expressed to the wearer, the receiver is present on or near the housing unit itself. Meanwhile, if the signal is being expressed to another user, such as a caregiver, through means such as a wireless radio, a computer device or a smart phone, the transmitter may send a wireless signal to a receiver located some distance away from the transmitter and signaling device. The signal may be deactivated remotely or at or near the absorbent article.

Figure 3:
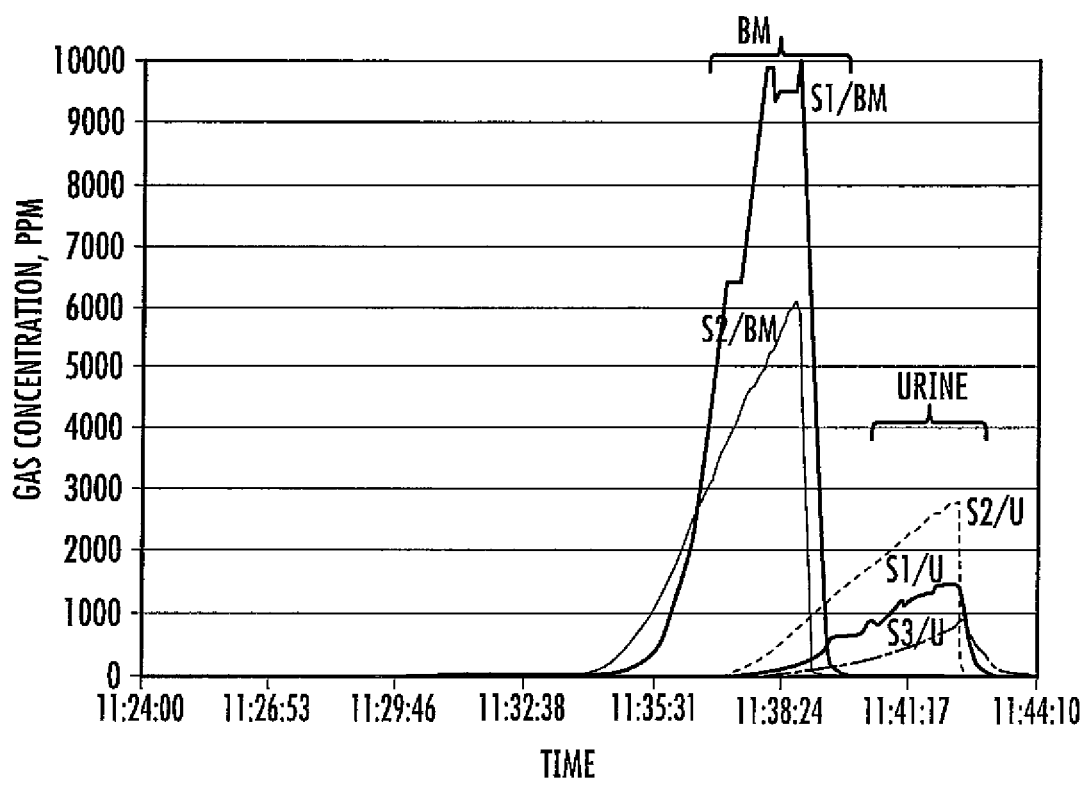
FIG. 3 is a graph that is representative of various non-contact electronic sensor array outputs that can be used to determine if an insult of urine, bowel movement or both has occurred within or on an absorbent article.

FIG. 3 shows the data that an embodiment of an electronic sensor array can collect. The graph shows gas concentrations monitored by one embodiment of the non-contact electronic sensor array. The output concentration levels vary for a fecal or bowel movement insult (labeled "BM" for bowel movement insult on the graph) and a urine insult as shown by the different levels of gas present in each of the gas samples. The gas concentrations can be detected by rising above a minimum threshold level after each of the individual sensors or the sensor array were calibrated and zeroed outside the presence of an insult. The graph shows the gas levels monitored by at least one sensor. It should be pointed out here that more than one sensor can be used within the non-contact electronic sensor array to detect urine insults and bowel movement insults within one embodiment. It should be noted that gas concentrations depend on diet, the amount of insult, as well as the time. The sensors are capable of detecting gas concentrations of a few parts per million (PPM) to thousands of PPM. Whether or not a potential insult within an absorbent article is a false alarm or not is decided by the controller. The gas sensors are only for reading the concentration values. A processor within the controller can determine whether a reading by the controller is an insult or a false alarm (e.g. flatulence) by analyzing the signal. For example, a gas concentration reading may be very high in the event of flatulence, but it diminishes in a very short amount of time compared gas concentration readings associated with an insult inside the absorbent article.

Figure 4:
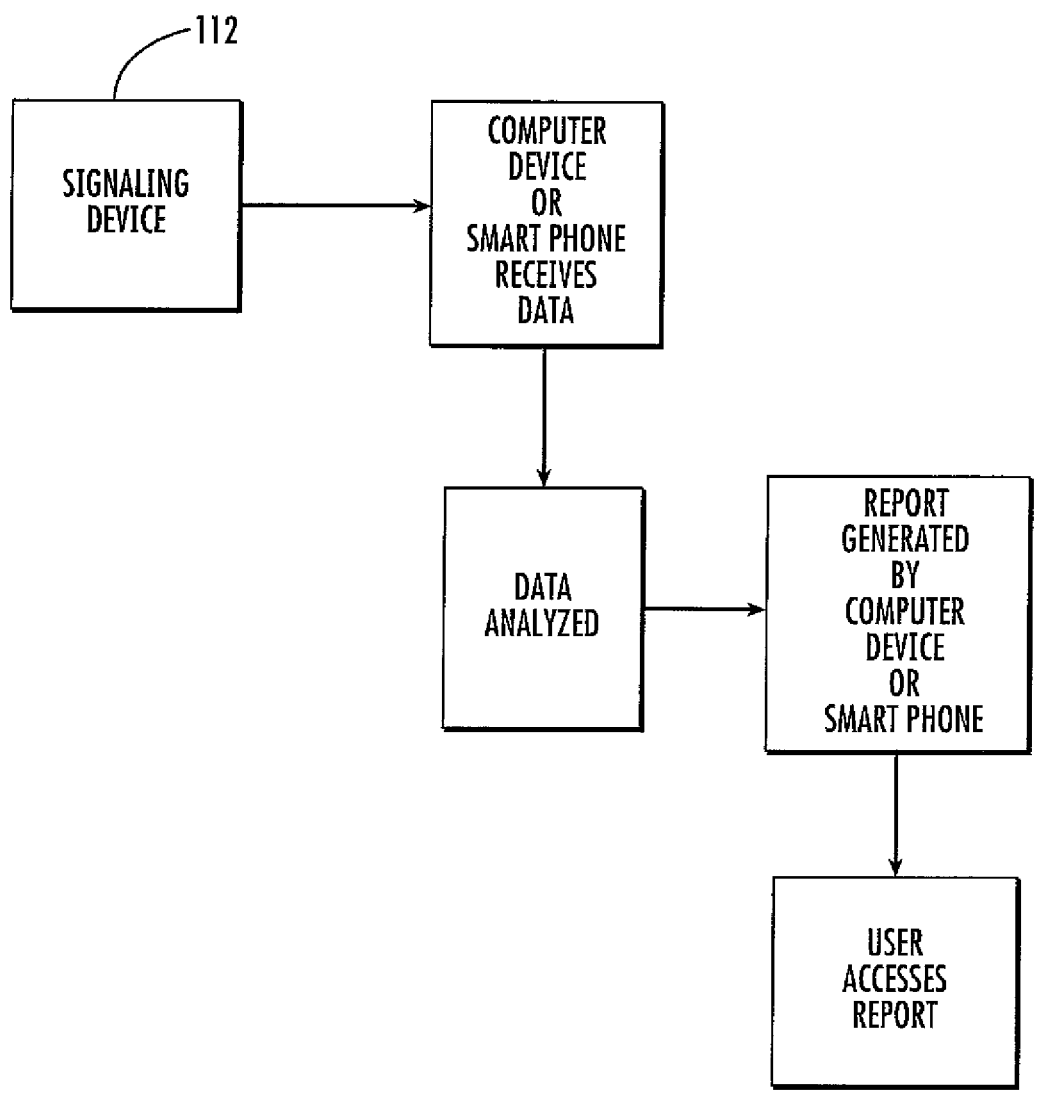
FIG. 4 is a block diagram showing how an embodiment of a signaling device can transmit data to a computer device or smart phone, which can then generate data reports for a user or caregiver to access.

FIG. 4 is a block diagram describing how a signaling device may connect with a computer device or smart phone, which can then generate data reports for the user to access. In one embodiment, after a non-contact electronic sensor array has monitored at least one gas level and a microcontroller has detected an increase above a threshold level through pattern recognition and data analysis to indicate the presence of a urine insult, a bowel movement insult, or both, a signaling device may transmit an alert to a location in close proximity to the absorbent article, such as near the waist opening of an absorbent article or at the edge of an absorbent article to inform the wearer or a caregiver who is close by. In another embodiment, the user or caregiver may wish to receive an alert at a remote location, such as via a wireless radio. In still another embodiment, the user or caregiver may wish to have the alerts sent to a computer device or smart phone. When sent to a computer device or smart phone, the alert may be visual or auditory, or the alert may be stored as data along with previous and future alerts. In this manner, the user or caregiver may be able to call up the data from the computer device or smart phone to determine the number and type of insults within an absorbent article that is being monitored. The user or caregiver can view a report generated on a computer device or smartphone that was transmitted to the computer device or smartphone from the signaling device and can access the report for various uses.

Different attachment mechanisms for attaching the housing unit containing the non-contact electronic sensor array, controller and signaling device to the absorbent article will now be described in detail with respect to FIGS. 5 and 6. It should be noted that while the attachment mechanisms shown in the figures below generally incorporate two plates or sides, the non-contact electronic sensor array 104 can be positioned in one embodiment so that it is on a plate or side facing the interior or absorbent layer of the absorbent article in order to be able to detect gases due to a urine and/or bowel movement insult.

Figure 5:
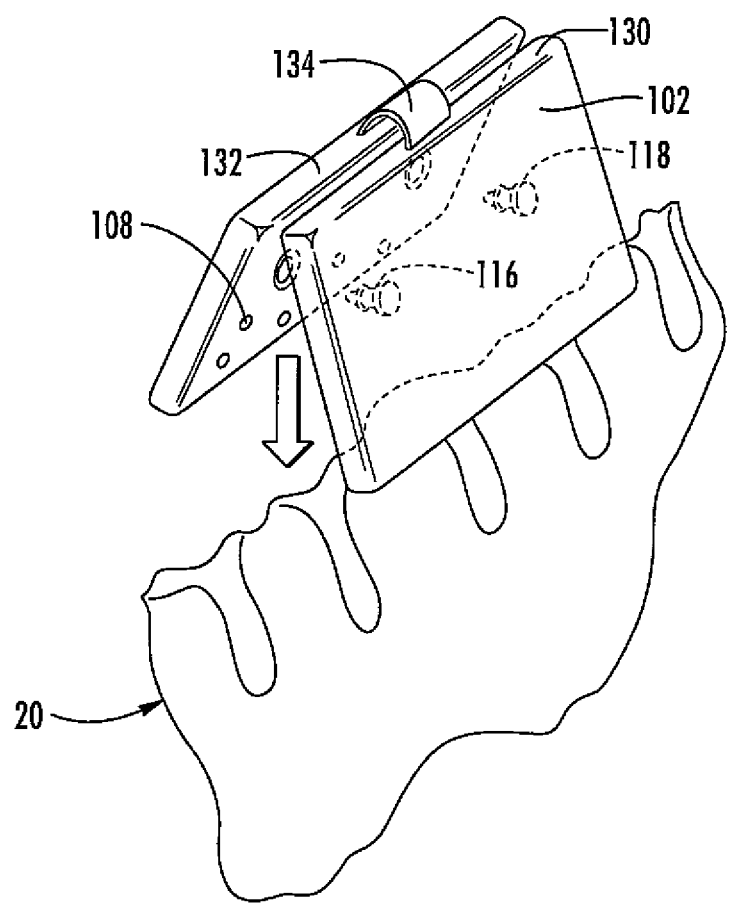
FIG. 5 is an embodiment of an attachment mechanism for attaching a housing unit to an absorbent article in accordance with the present disclosure.

Referring to FIG. 5, an embodiment of an attachment mechanism that may be used to attach the housing unit 102 to an absorbent article 20 is shown. In this embodiment, the housing unit 102 comprises a first exterior plate 130 spaced from a second interior plate 132. The first exterior plate 130 should be placed on the outside or non-absorbent portion of the absorbent article 20. In one embodiment, the second interior plate 132 can be placed on the inside or absorbent portion of the absorbent article 20 so that the gases emitted from the absorbent article 20 after an insult will be able to reach the openings 108. Once the gases reach the openings 108 in the housing unit 102, then the non-contact electronic sensor array 104 can monitor gas concentration levels, and then the controller 106 can detect any changes in the gas concentration levels due to an insult. Note also that the non-contact electronic sensor array 104 can monitor changes in temperature and humidity that the controller 106 may then detect. Additionally, an end of the first exterior plate 130 may be pivotally connected to an end of the second interior plate 132 about a hinge 134.

In order to attach the housing unit 102 to the absorbent article 20, the first exterior plate 130 includes a pair of prongs that serve as the first terminal 116 and the second terminal 118. As shown in the drawing, the plates 130 and 132 of the housing unit 102 are configured to be placed over an edge of the chassis, such as about a waist opening, and brought together such that the prongs 116 and 118 pierce the chassis and lock into place. Note, however, that the plates may also be placed over the edge of an absorbent article, such as a bed pad or mat.

Figure 6:
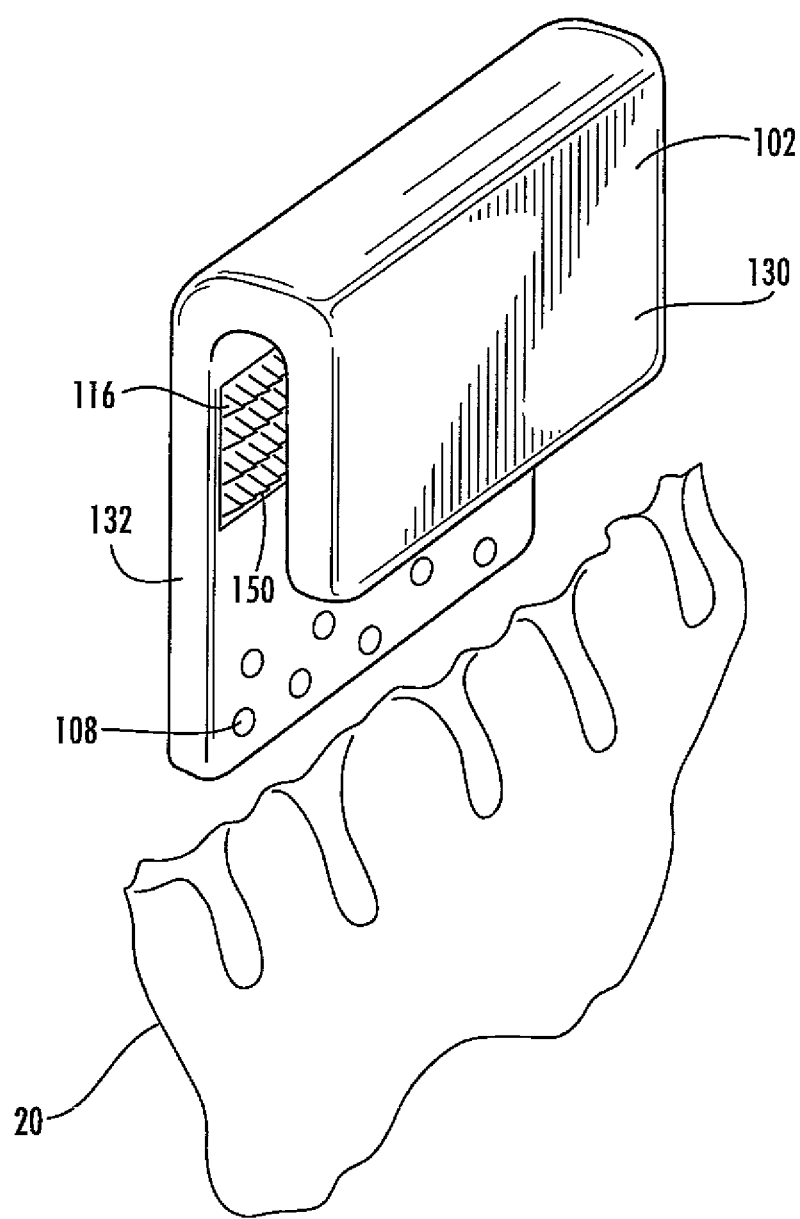
FIG. 6 is another embodiment of an attachment mechanism for attaching a signaling device to an absorbent article in accordance with the present disclosure.

Referring to FIG. 6, still another embodiment of a housing unit 102 connected to an absorbent article 20 is shown. In this embodiment, the housing unit 102 may include a clip device comprising a first exterior plate 130 spaced from a second interior plate 132. The plates 130 and 132 are integral with each other and are made from a flexible material that allows the plates to be separated from each other for placing the signaling device over an edge on an absorbent article. Once the plates, however, are placed on the absorbent article, the plates are biased towards each other for holding the signaling device in place. In this manner, the housing unit 102 has a paper clip-like structure. In this manner, the housing unit 102 may be positioned securely to the absorbent article. Note that the plates shown are connected to the waist opening of an absorbent article, but they may also be placed over the edge of an absorbent article such as a bed pad or mat.

In one embodiment, placing the second interior plate 132 on the inside of the absorbent article 20 allows the gases emitted from the absorbent article 20 after an insult to reach the openings 108 in the housing unit 102. Once the gases reach the openings 108, then the non-contact electronic sensor array 104 can monitor gas concentration levels, and then the controller 106 can detect any changes in the gas concentration levels due to an insult.

In the embodiments illustrated in FIGS. 5 and 6, the housing unit 102 can be made from any suitable material. For example, in one embodiment, the housing unit can be made from a flexible plastic material. It should be understood, however, that elastomeric materials and metal materials may also be used. Additionally, at least a portion of the housing unit may be made of porous or mesh-like material to allow for the non-contact electronic sensor array to receive a sufficient gas sample to monitor gas levels above a threshold level.

As described above, the present disclosure is particularly directed to incorporating a body exudate indicating system that may be able to detect the presence of urine and/or bowel movement in the absorbent article 20. The remaining materials used to form the absorbent article 20 that surround the waist elastic members 54 and 56 may vary depending upon the particular application and the particular product being produced.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J., U.S.A. The liquid permeable outer layer can be any suitable material and is desirably one that provides a generally cloth-like texture. One example of such a material is a 20 gsm (grams per square meter) spunbonded polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure (not shown). A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The absorbent structure may be disposed between the outer cover 40 and the bodyside liner 42. The absorbent structure can be any structure or combination of components which are generally compressible, conformable, non-irritating to a wearer's skin, and capable of absorbing and retaining liquids and certain body wastes. For example, the absorbent structure may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 100 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, superabsorbent materials are available from Evonik Industries, Germany.

After being formed or cut into a desired shape, the absorbent web material may be wrapped or encompassed by a suitable tissue or meltblown web or the like wrap sheet that aids in maintaining the integrity and shape of the absorbent structure.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference to the extent they are consistent (i.e., not in conflict) herewith.

These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the disclosure so further described in such appended claims.

What is claimed is:

1. An absorbent article comprising:
   a chassis comprising an outer cover having an interior surface and an exterior surface and an absorbent structure positioned adjacent the interior surface of the outer cover;
   a non-contact electronic sensor array, the non-contact electronic sensor array comprising a plurality of gas sensors, wherein the non-contact electronic sensor array monitors gas concentration levels of gases emitted by two or more volatile compounds within the absorbent article, wherein each sensor in the non-contact electronic sensor array identifies a particular gas;
   a controller configured to detect changes above a threshold level in the gas concentration levels of the plurality of gas sensors within the non-contact electronic sensor array as the result of an insult within the absorbent article, wherein the insult is a urine insult, a bowel movement insult, or a combination thereof; and
   a signaling device that alerts a user of changes in the gas concentration levels detected by the controller via an alert and discriminates between a urine insult and a bowel movement insult, wherein the alert is deactivated at or near the absorbent article or remotely from a smart phone or computer.

2. An absorbent article as defined in claim 1, further comprising a housing unit, wherein the housing unit comprises the non-contact electronic sensor array, the controller and the signaling device.

3. An absorbent article as defined in claim 2, wherein the housing unit is in close proximity to the chassis of the absorbent article, wherein the non-contact electronic sensor array detects the presence of gases within or around the absorbent article after an insult of urine, bowel movement, or combinations thereof.

4. An absorbent article as defined in claim 1, wherein the non-contact electronic sensor array monitors gas concentration levels of fatty alcohols, small chain fatty acids, and sulfur compounds.

5. An absorbent article as defined in claim 4, wherein the non-contact electronic sensor array monitors gas concentration levels associated with ammonia, thiols, and indole.

6. An absorbent article as defined in claim 1, comprising a gas emitting substance, wherein the gas emitting substance emits a gas after an insult within the absorbent article, and wherein the non-contact electronic sensor array monitors gas concentration levels of the gas emitting substance within the absorbent article.

7. An absorbent article as defined in claim 1, wherein the non-contact electronic sensor array monitors changes in humidity and temperature within the absorbent article.

8. An absorbent article as defined in claim 1, wherein the alert is selected from an auditory signal, a vibratory signal, a visual signal, or combinations thereof.

9. An absorbent article as defined in claim 8, wherein the signaling device generates an alert that is transmitted wirelessly to a radio at a remote location.

10. An absorbent article as defined in claim 1, wherein the signaling device generates an alert that is transmitted to at least one computer device or smart phone, wherein the computer device or smart phone is adapted to receive data from the signaling device, generate at least one report utilizing at least a portion of the data, and provide a user access to the data and the at least one report.

11. An absorbent article as defined in claim 1, wherein the volatile compounds are acetic acid, ammonia, methane, hydrogen sulfide, dimethyl sulfide, skatole, thiols, indole or combinations thereof.

12. An absorbent article comprising:
    a chassis comprising an outer cover having an interior surface and an exterior surface and an absorbent structure positioned adjacent the interior surface of the outer cover;
    a gas emitting substance, wherein the gas emitting substance emits a gas after an insult within the absorbent article;
    a non-contact electronic sensor array, the non-contact electronic sensor array comprising a plurality of gas sensors, wherein the non-contact electronic sensor array monitors gas concentration levels of the gas emitting substance within the absorbent article, wherein each sensor in the non-contact electronic sensor array identifies a particular gas;
    a controller configured to detect changes above a threshold level in the gas concentration levels of the plurality of gas sensors within the non-contact electronic sensor array as the result of an insult within the absorbent article, wherein the insult is a urine insult, a bowel movement insult, or a combination thereof; and
    a signaling device that alerts a user of changes in the gas concentration levels detected by the controller via an alert and discriminates between a urine insult and a bowel movement insult, wherein the alert is deactivated at or near the absorbent article or remotely from a smart phone or computer.

13. An absorbent article as defined in claim 12, further comprising a housing unit, wherein the housing unit comprises the non-contact electronic sensor array, the controller and the signaling device.

14. An absorbent article as defined in claim 13, wherein the housing unit is in close proximity to the chassis of the absorbent article, wherein the non-contact electronic sensor array detects the presence of gases within or around the absorbent article.

15. An absorbent article as defined in claim 12, wherein the signaling device generates an alert selected from the group consisting of an auditory signal, a vibratory signal, a visual signal, and combinations thereof.

16. An absorbent article as defined in claim 15, wherein the signaling device generates an alert that is transmitted wirelessly to a radio at a remote location.

17. An absorbent article as defined in claim 12, wherein the signaling device generates an alert that is transmitted to at least one computer device or smart phone, wherein the computer device or smart phone is adapted to receive data from the signaling device, generate at least one report utilizing at least a portion of the data, and provide a user access to the data and the at least one report.

18. A signaling device comprising:
   a non-contact electronic sensor array, the non-contact electronic sensor array comprising a plurality of gas sensors, wherein the non-contact electronic sensor array monitors gas concentration levels of gases emitted by volatile compounds, a gas emitting substance, or combinations thereof within an absorbent article, wherein each sensor in the non-contact electronic sensor array identifies a particular gas; and
   a controller configured to detect changes above a threshold level in the gas concentration levels of the plurality of gas sensors within the non-contact electronic sensor array as the result of an insult within the absorbent article, wherein the insult is a urine insult, a bowel movement insult, or a combination thereof;
   wherein the signaling device alerts a user of changes in the gas concentration levels detected by the non-contact electronic sensor array;
   wherein the signaling device is contained in a housing unit, wherein the housing unit is in close proximity to the absorbent article;
   wherein the signaling device generates at least one alert selected from an auditory signal, a vibratory signal, a visual signal, or combinations thereof and discriminates between a urine insult and a bowel movement insult;
   wherein the signaling device transmits the at least one alert remotely to a radio, a computer device, a smart phone, or combinations thereof, wherein the computer device or smart phone is adapted to receive data from the signaling device, generate at least one report utilizing at least a portion of the data, and provide a user access to the data and the at least one report; and
   wherein the at least one alert is deactivated at or near the absorbent article or remotely from a smart phone or computer.

\* \* \* \* \*